(12) United States Patent
Weitzmann et al.

(10) Patent No.: US 9,301,945 B2
(45) Date of Patent: Apr. 5, 2016

(54) METHODS FOR TREATING INFLAMMATORY CONDITIONS AND STATES, AND CANCERS BY ANTAGONIZING NF-κB ACTIVATION

(75) Inventors: M. Neale Weitzmann, Decatur, GA (US); Masayoshi Yamaguchi, Shizuoka (JP)

(73) Assignee: Emory University, Atlanta, GA (US)

( * ) Notice: Subject to any disclaimer, the term of this patent is extended or adjusted under 35 U.S.C. 154(b) by 76 days.

(21) Appl. No.: 14/234,033

(22) PCT Filed: Jul. 19, 2012

(86) PCT No.: PCT/US2012/047323
§ 371 (c)(1),
(2), (4) Date: Jan. 21, 2014

(87) PCT Pub. No.: WO2013/013003
PCT Pub. Date: Jan. 24, 2013

(65) Prior Publication Data
US 2014/0163093 A1   Jun. 12, 2014

Related U.S. Application Data

(60) Provisional application No. 61/510,169, filed on Jul. 21, 2011.

(51) Int. Cl.
  *A61K 31/381* (2006.01)
  *A61K 45/06* (2006.01)
  *A61K 33/24* (2006.01)
(52) U.S. Cl.
  CPC ............... *A61K 31/381* (2013.01); *A61K 33/24* (2013.01); *A61K 45/06* (2013.01)
(58) Field of Classification Search
  CPC ............................. A61K 31/381; A61K 45/06
  USPC ........................................................ 514/447
  See application file for complete search history.

(56) References Cited

U.S. PATENT DOCUMENTS

| | | | |
|---|---|---|---|
| 5,128,367 A | 7/1992 | Wierzbicki et al. | |
| 7,214,805 B2 | 5/2007 | Vaysse-Ludot et al. | |
| 7,459,568 B2 | 12/2008 | Horvath et al. | |
| 2006/0122274 A1* | 6/2006 | Hansen et al. | 514/566 |
| 2007/0292529 A1* | 12/2007 | Tabbiner | 424/601 |
| 2008/0317849 A1* | 12/2008 | Christgau et al. | 424/464 |

OTHER PUBLICATIONS

Meunier et al. The Effects of Strontium Ranelate on the Risk of Vertebral Fracture in Women with Postmenopausal Osteoporosis (2004) N Engl J Med 350(5): 459-468.
Reginster et al. Strontium Ranelate Reduces the Risk of Nonvertebral Fractures in Postmenopausal Women with Osteoporosis: Treatment of Peripheral Osteoporosis (TROPOS) Study(2005) J Clin Endocrinol Metab 90(5): 2816-2822.
Porter Use of Strontium-89 in Metastatic Cancer: US and UK Experience, Oncology 1994.
NPS, Strontium ranelate (Protos)—for osteoporosis in postmenopausal women, 2008.
Fromique et al. Essential role of nuclear factor of activated T cells (NFAT)-mediated Wnt signaling in osteoblast differentiation induced by strontium ranelate. 2010, J Biol Chem 285(33): 25251-25258.
Caudrillier et al. Strontium ranelate decreases receptor activator of nuclear factor-KB ligand-induced osteoclastic differentiation in vitro: involvement of the calcium-sensing receptor. Mol Pharmacol, 2010, 78(4):569-76.
Li et al., Endogenous TNF alpha Lowers Maximum Peak Bone Mass and Inhibits Osteoblastic Smad Activation Through NF-kB, J Bone Miner Res, 2007, 22(5): 646-655.

* cited by examiner

*Primary Examiner* — Raymond Henley, III
(74) *Attorney, Agent, or Firm* — Emory Patent Group

(57) ABSTRACT

The disclosure is directed to methods for treating inflammatory conditions and cancers that have misregulated NF-κB. In some embodiments, the disclosure is directed to methods for treating inflammatory conditions, inflammatory states associated with treating HIV and AIDS infections, and cancers that include administering strontium ranelate to a subject diagnosed with or at risk of inflammatory conditions, inflammatory states, and cancers, respectively.

9 Claims, 7 Drawing Sheets

A

B

A

B

METHODS FOR TREATING INFLAMMATORY CONDITIONS AND STATES, AND CANCERS BY ANTAGONIZING NF-κB ACTIVATION

CROSS REFERENCE TO RELATED APPLICATION

This application claims priority to U.S. Provisional Application No. 61/510,169 filed Jul. 21, 2011, hereby incorporated by reference in its entirety.

BACKGROUND

Strontium ranelate, a divalent strontium salt of ranelic acid, possesses a capacity to both stimulate bone formation and repress bone resorption. Strontium ranelate has been shown in clinical trials to protect against bone loss and to reduce fracture risk in postmenopausal women by both stimulating bone formation and simultaneously suppressing bone resorption. See Meunier et al. (2004) N Engl J Med 350(5): 459-468; and Reginster et al. (2005) J Clin Endocrinol Metab 90(5): 2816-2822. However, the molecular processes by which this is accomplished are poorly characterized.

NF-κB (nuclear factor kappa-light-chain-enhancer of activated B cells) is a protein complex that controls the transcription of DNA. NF-κB is widely used by eukaryotic cells as a regulator of genes that control cell proliferation and cell survival. NF-κB is well established to be critical for osteoclast development, function and survival. NF-κB also controls many genes involved in inflammation. NF-κB has been found to be chronically active in many inflammatory diseases, such as inflammatory bowel disease, arthritis, sepsis, gastritis, asthma, among others.

SUMMARY

The disclosure relates to methods for treating a condition associated with misregulated NF-κB such as inflammation or cancer. In some embodiments, the disclosure relates to a method of treating an inflammatory condition or state comprising administering strontium ranelate to a subject, at risk of, exhibiting symtoms of, or diagnosed with an inflammatory condition or state.

In further embodiments, the inflammatory condition may include any one of ulcerative colitis [UC], Crohn's disease [CD], rheumatoid arthritis, systemic lupus erythematosus, psoriatic arthritis, giant cell arthritis, type 1 diabetes, multiple sclerosis, celiac disease, and Parkinson's disease. In other embodiments, the inflammatory state may include any one of bone loss or inflammation. The inflammatory state may be associated with any one of Human Immunodeficiency Virus (HIV) infection, Acquired Immune Deficiency Syndrome (AIDS) infection, or treatment thereof, including antiretroviral therapy. In some embodiments, a low dose of strontium ranelate may be administered. In some embodiments, the administering the strontium ranelate induces a therapeutic effect. In some embodiments, the therapeutic effect may be antagonization of NF-κβ activation. In some embodiments, the therapeutic effect may be induced by a low dose of strontium ranelate. In some embodiments, daily doses of strontium ranelate may be between 1 mg to 10 mg, 10 mg to 50 mg, 60 mg to 100 mg, 100 mg to 500 mg, 500 mg to 2 g, or 2 g to 4 g. In further embodiments, strontium ranelate is administered in combination with a different agent. In some embodiments, the different agent is a different anti-inflammatory agent.

In some embodiments, the disclosure relates to a method of treating a cancer comprising administering strontium ranelate to a subject diagnosed with cancer. In some embodiments, the cancer may include any one of oral squamous cell carcinoma, colorectal cancer, hepatocellular carcinoma, breast cancer and myeloma. In other embodiments, the cancer may be a cancerous tumor located in any one of breast, brain, gastrointestinal tract, liver, lung, bladder, pancreas, prostate, and ovary.

In some embodiments, the administering the strontium ranelate induces a therapeutic effect. In some embodiments, the therapeutic effect may be antagonization of NF-κB activation. In some embodiments, the therapeutic effect may be induced by a low dose of strontium ranelate. In some embodiments, daily doses of strontium ranelate may be between 1 mg to 10 mg, 10 mg to 50 mg, 60 mg to 100 mg, 100 mg to 500 mg, 500 mg to 2 g, or 2 g to 4 g. In further embodiments, strontium ranelate may be administered in combination with a different agent. In some embodiments, the different agent is a different anti-inflammatory agent.

In certain embodiments, the disclosure relates to uses of strontium ranelate in the production of a medicament for the treatment of inflammatory and other conditions disclosed herein.

BRIEF DESCRIPTION OF FIGURES

FIG. 1A shows MC3T3 cells that were cultured in control or mineralizing medium in the presence of absence of 200 µM of strontium ranelate (SrRa), strontium chloride (SrCl) or sodium ranelate (NaRa) for 17 days and mineral deposition visualized by Alizarin-red S staining.

FIG. 5A shows RAW264.7 osteoclast precursors that were induced to differentiate into osteoclasts with RANKL (30 ng/ml) in the presence or absence of strontium ranelate (SrRa) in the range 1 to 200 µM. Cultures were stained with TRAP 7 days later and osteoclasts (TRAP+ multinucleated (≥3 nuclei)) cells quantitated.

FIG. 6A shows RAW264.7 osteoclast precursors that were induced to differentiate into osteoclasts with RANKL (30 ng/ml) in the presence or absence of 10 or 100 µM strontium ranelate (SrRa), strontium chloride (SrCl2), or sodium ranelate (NaRa). Cultures were stained with TRAP 7 days later and osteoclasts (TRAP+ multinucleated (>3 nuclei)) cells quantitated. Data is expressed as mean±SD of 6 replicate wells per data set, and representative of 2 independent experiments. ***p<0.001 versus RANKL stimulated only (grey bar), 1 way ANOVA, Tukey-Kramer post test.

DETAILED DESCRIPTION

Terms

Figure 1:
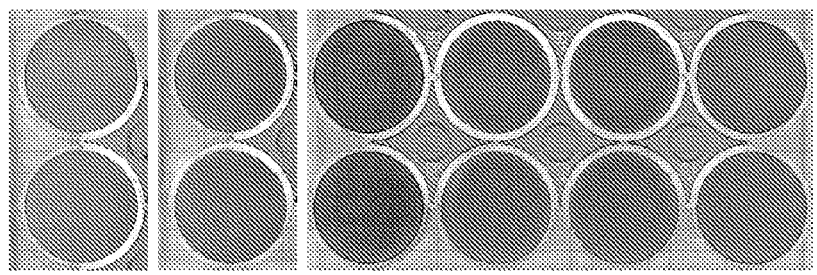
FIGS. 1A and B show the effect of strontium ranelate, strontium chloride and sodium ranelate on mineralization of MC3T3 osteoblast precursors and TNFα-induced suppression of mineralization in vitro.
FIG. 1B shows MC3T3 cells that were cultured in control or mineralizing medium in the presence of absence of the osteoblast differentiation inhibitor TNFα (5 ng/ml). Parallel TNFα treated wells received a dose range of strontium ranelate (SrRa) from 10 to 200 All wells in each experiment are form the same plate but were digitally separated and reorganized for clarity. Non-contiguous wells were separated by a white space to indicate this fact. Data is representative of 2 independent experiments.
Figure 1:
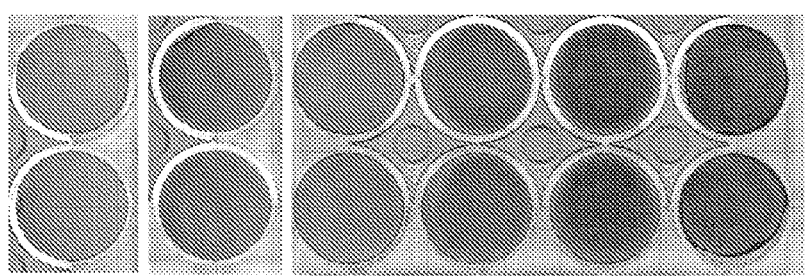

To facilitate understanding of embodiments of the disclosure, a number of terms are defined below.

The term "therapeutically effective amount" as used herein refers to that amount of the compound being administered which will relieve to some extent one or more of the symptoms of the disorder being treated. In reference to cancer or pathologies related to increased cell division and inflammation, a therapeutically effective amount refers to that amount which has the effect of (1) suppressing (that is, preventing to some extent, preferably stopping) NF-κB activation, (3) relieving to some extent (or, preferably, eliminating) one or more symptoms associated with a pathology related to or caused in part by inflammation, and/or (4) preventing the chain of events downstream of inflammation which leads to the pathology.

A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, the terms "treat" and "treating" are not limited to the case where the subject (e.g., patient) is cured and the disease is eradicated. Rather, embodiments of the present disclosure also contemplate treatment that merely reduces symptoms and/or delays disease progression.

The term "therapeutic effect" refers to the inhibition of an abnormal condition. A therapeutic effect relieves to some extent one or more of the symptoms of the abnormal condition. In reference to the treatment of abnormal conditions, a therapeutic effect can refer to one or more of the following: (a) an increase or decrease in the proliferation, growth, and/or differentiation of cells; (b) inhibition (i.e., slowing or stopping) of growth of tumor cells in vivo (c) promotion of cell death; (d) inhibition of degeneration; (e) relief to some extent of one or more of the symptoms associated with the abnormal condition; and (f) enhancement of the function of a population of cells.

The term "inflammatory condition" refers to a disease that is characterized by inflammation. The inflammatory condition may include, but not limited to: atherosclerosis, ulcerative colitis [UC], Crohn's disease [CD], rheumatoid arthritis, systemic lupus erythematosus, psoriatic arthritis, giant cell arthritis, type 1 diabetes, multiple sclerosis, celiac disease, and Parkinson's disease.

The term "inflammatory state" refers to a state of inflammation that is characterized by bone loss or inflammation. The inflammatory state may be associated with any one of HIV infection, AIDS infection, or treatment thereof. Treatment may include, but not limited to, antiretroviral therapy.

A "subject" refers to any animal such as a human patient, livestock or a domestic pet.

As used herein "cancer" refers any of various cellular diseases with malignant neoplasms characterized by the proliferation of cells. Most cancers form a tumor but some, like leukemia, do not. It is not intended that the diseased cells must actually invade surrounding tissue and metastasize to new body sites. Cancer can involve any tissue of the body and have many different forms in each body area. Examples of cancer, may include, but are not limited to, oral squamous cell carcinoma, colorectal cancer [CRC], hepatocellular carcinoma, leukemia, lymphoma, glioma, and myeloma, as well as cancers of the bone, breast, neck, brain, gastrointestinal tract, liver, lung, bladder, pancreas, prostate, and ovary, as well as their metastases to bone and other sites.

Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed. It may also be identified by a change in relevant biomarker or gene expression profile, such as HER2 for breast cancer.

Cancers may be diagnosed by well-known methods in the art. For example, breast cancer is commonly diagnosed using a "triple test," i.e., clinical breast examination, mammography, and fine needle aspiration and cytology. Fine needle aspiration and cytology (FNAC) involves extracting a small portion of fluid from a lump. Clear fluid makes the lump unlikely to be cancerous. Bloody fluid may be sent off for inspection under a microscope for cancerous cells. Other options for biopsy include core biopsy, where a section of the breast lump is removed, and an excisional biopsy, where the entire lump is removed.

Some breast cancers require the hormones estrogen and progesterone to grow. After surgery these cancers are typically treated with drugs that interfere with hormones, such as tamoxifen, and with drugs that shut off the production of estrogen in the ovaries or elsewhere. After surgery, low-risk, hormone-sensitive breast cancers may be treated with hormone therapy and radiation. Another breast cancers regimen is cyclophosphamide plus doxorubicin (Adriamycin), referred to as CA. Sometimes a taxane, such as docetaxel, is added, and the regime is then referred to as CAT. An alternative treatment is cyclophosphamide, methotrexate, and fluorouracil (CMF). Therapeutic antibodies, such as trastuzumab (Herceptin), are typically used for cancer cells that over express the HER2. It is contemplated that methods disclosed herein may be used in combination with any of the regiments described above.

As used herein, the term "about" refers to an approximation of a stated value within an acceptable range. Preferably, the range is +/−5% of the stated value.

"Strontium ranelate" is composed of an organic moiety and is a strontium (II) salt of ranelic acid. Strontium ranelate is a distrontium salt of 2-[N,N-di(carboxymethyl)amino]-3-cyano-4-carboxymethylthiophene-5-carboxylic acid, and is described in, for example, U.S. Pat. No. 5,128,367, U.S. Pat. No. 7,459,568, and U.S. Pat. No. 7,214,805, which are hereby incorporated by reference in their entireties.

The terms "including," "such as," "for example," and the like are intended to refer to exemplary embodiments and not to limit the scope of the present disclosure.

DETAILED DISCUSSION

Disclosed herein are investigations of the processes associated with the stimulation of bone formation and the suppression of bone resorption. The findings indicate that suppression of NF-κB is the centralized mechanism that achieves these actions by regulating both osteoclasts and osteoblasts. The findings further indicate that strontium ranelate may reverse the suppressive action of TNFα on mineralization in vitro. TNFα is a pro-inflammatory cytokine that plays a role in the pathology of multiple osteoporotic conditions, including postmenopausal osteoporosis and rheumatoid arthritis. Given the capacity of strontium ranelate to antagonize TNFα-induced NF-κB activity in osteoblasts, the anabolic effects of this compound in vivo may be achieved, at least in part, by suppressing NF-κB-activation induced by TNFα and other inflammatory cytokines in postmenopausal women.

In vivo, basal TNFα levels reach a magnitude capable of suppressing basal bone formation and lowering peak bone mineral density in mice and that suppression of basal NF-κB activity in osteoblasts, using a specific inhibitor, upregulates osteoblast differentiation in vitro even in the absence of any exogenous NF-κB agonists. See, e.g., Li et al. (2007) J Bone Miner Res 22(5): 646-655. Consistently, strontium ranelate was observed to promote a robust osteoblast mineralization even in the context of unstimulated in vitro cultures. The NF-κB reporter assays used in the investigations provide evidence of a high rate of basal NF-κB activity in osteoblast precursors that may explain the capacity of strontium ranelate to augment MC3T3 mineralization under unstimulated conditions.

The high basal activity may be explained by that the FBS necessary to culture the cells may contain NF-κB activators. Alternatively, osteoblasts may maintain an intrinsically high basal NF-κB state that may act as a natural barrier to spontaneous osteoblast precursor differentiation, thus maintaining the pluripotency of the lineage.

TGFβ is an important early commitment factor for osteoblast differentiation and for targeting and recruitment of osteoblast precursors to sites of bone resorption. See Janssens et al. (2005) Endocr Rev 26(6): 743-774; and Tang et al. (2009) Nat Med 15(7): 757-765. The findings also reveal that strontium ranelate significantly alleviates the suppressive effect of TNFα on TGFβ-induced Smad activation in osteoblast precursors. Strontium ranelate showed no direct effects on Smad activity and its action is thus likely mediated solely though antagonism of TNFα-driven NF-κB activation.

In contrast to osteoblasts, strontium ranelate was found to potently antagonize RANKL-induced NF-κB activation in osteoclast precursors without evidence of anti-proliferative or direct toxic effects. NF-κB activation is critical to osteoclast differentiation and activity and blunting NF-κB activation could account, in part, for the anti-osteoclastogenic activity of this compound in vivo.

Disclosed herein are also investigations of the role of intact strontium ranelate relative to that the strontium component of the complex. It has long been believed that the biological activity of strontium ranelate is solely a consequence of the dissociation of the complex in vivo releasing strontium ions that are preferentially targeted to bone and the bone microenvironment. In fact, based on this assumption, multiple varieties of strontium containing molecules are now being widely touted as effective anti-osteoporotic supplements. However, the findings suggest that the anti-NF-κB activity and anti-osteoclastogenic effects and pro-osteoblastic effects of low dose strontium ranelate may be a direct consequence of the intact complex, rather than the strontium moiety. This data appears to contrast with other studies such as that of Fromigue et al. (2010) J Biol Chem 285(33): 25251-25258, who reported that addition of a mixture of strontium chloride and sodium ranelate to culture medium at a molar ratio of 1:100, was biologically active in MC3T3 cells and stimulated NFAT translocation and Wnt transcription, leading to induction of an osteoblastic gene program. In the investigations, discussed below, however, strontium ion concentrations were titrated to 1 or 3 mM. In the studies herein, strontium ranelate achieved significant biological activities at doses as low as 1 μM and was saturating at 100 μM in the in vitro osteoblast differentiation and mineralization assays. This low dose is effective even in the presence of the osteoblast inhibitor TNFα.

By contrast, no significant effect of strontium chloride on NF-κB activity at doses up to 1 mM was observed. The investigations suggest that in contrast to the potential actions of high dose strontium on osteoblast differentiation, low doses of intact strontium ranelate may further mediate potent effects on osteoblast and osteoclast differentiation, by antagonizing NF-κB activation. The net effects on bone turn-over in vivo are likely thus a combination of multiple mechanisms mediated though both intact strontium ranelate and its metabolites.

The findings also provide a novel mechanism to explain, in part, the dual pro-anabolic and anti-catabolic activities of strontium ranelate, and further support the concept that pharmacological modulation of the NF-κB signal transduction may constitute an effective mechanism for ameliorating pathological bone loss.

I. Therapeutic Uses

The present disclosure provides a method that includes administering a therapeutic amount of strontium ranelate to treat or prevent the following:

(a) inflammatory conditions, including, but not limited to: atherosclerosis, ulcerative colitis [UC], Crohn's disease [CD], rheumatoid arthritis, systemic lupus erythematosus, psoriatic arthritis, giant cell arthritis, type 1 diabetes, multiple sclerosis, celiac disease, and Parkinson's disease;

(b) inflammatory states, including but not limited to: bone loss and inflammation that may be associated with HIV infection or AIDS infection, as well as the treatment thereof, such as antiretroviral therapy;

(c) abnormal cell growth, including, but not limited to: oral squamous cell carcinoma, colorectal cancer [CRC], hepatocellular carcinoma, breast cancer, myeloma, and tumors including cancers of the bone, breast, brain, gastrointestinal tract, liver, lung, bladder, pancreas, prostate, and ovary, as well as their metastases to bone and other sites; and (d) skeletal fractures.

Given its action on NF-κB signal transduction, in some embodiments, strontium ranelate may be an effective antiosteoporotic agent to treat inflammatory conditions including rheumatoid arthritis. Pharmacological suppression of NF-κB activation is reported to ameliorate bone erosions in an in vivo animal model of rheumatoid arthritis. See, e.g., Dai et al. (2004) J Biol Chem 279(36): 37219-37222. In addition, as the NF-κB pathway plays important roles in driving inflammation, in other embodiments, strontium ranelate may be used to treat inflammation.

In other embodiments, strontium ranelate may treat inflammation and inflammation-associate sequelae. Strontium ranelate may have additional indirect benefits in relieving inflammation and inflammation-associated sequelae, such as skeletal deterioration as a consequence of potential anti-inflammatory properties.

In other embodiments, strontium ranelate may be used to treat fracture repair. Recent studies report that pharmacological suppression of TNFα reverses age-related defects in bone formation in a mouse fracture healing model. See, e.g., Wahl et al. (2010) J Bone Miner Res 25(1): 114-123.

II. Combination Therapy

The combination therapy may be administered as (a) a single pharmaceutical composition that comprises strontium ranelate; or (b) two separate pharmaceutical compositions comprising (i) a first composition comprising strontium ranelate and a pharmaceutically acceptable excipient, diluent, or carrier, and (ii) a second composition comprising at least one additional pharmaceutical agent, such as those described herein, and a pharmaceutically acceptable excipient, diluent, or carrier. The pharmaceutical compositions may be administered simultaneously or sequentially and in any order.

In use in treating or preventing inflammatory conditions or states described herein, strontium ranelate may be administered together with at least one other anti-inflammatory agent as part of a unitary pharmaceutical composition. Alternatively, strontium ranelate may be administered apart from the other anti-inflammatory agent. In one embodiment, strontium ranelate and the at least one other anti-inflammatory agent may be administered substantially simultaneously, i.e., the compounds are administered at the same time or one after the other, so long as the compounds reach therapeutic levels for a period of time in the blood.

Combination therapy involves administering strontium ranelate, as described herein, in combination with at least one anti-inflammatory agent, ideally one which functions by a different mechanism.

Suitable anti-inflammatory compounds and agents include both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasonephosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, and triamcinolone. Mixtures of the above steroidal anti-inflammatory compounds may also be used.

Non-limiting examples of non-steroidal anti-inflammatory compounds and agents include nabumetone, celecoxib, etodolac, nimesulide, apasone, gold, oxicams, such as piroxicam, isoxicam, meloxicam, tenoxicam, sudoxicam, the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

Combination therapy involves administering strontium ranelate, as described herein, in combination with at least one more anti-cancer agent, ideally one which functions by a different mechanism. Examples of anti-cancer agents contemplated by the disclosure include docetaxel, cis-platin, 5-fluorouracil, tegafur-uracil, capecitabine, leucovorin, oxaliplatin, irinotecan, panitumumab, oblimersen, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin bortezomib, anegrilide, tamoxifen, toremifene, raloxifene, droloxifene, iodoxyfene fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, gefitinib, erlotinib, dasatinib, imatinib, bevacizumab, combretastatin, thalidomide, and lenalidomide.

Examples of agents that may also be used for combination therapy include, but are not limited to, non-steroidal anti-inflammatory drugs, steroids, anticoagulants, antithrombotic drugs, antibacterial agents, antifungal agents, antivirus drugs, thrombolytic drugs, methemoglobin increase preventive drugs, immunomodulators, antiprotozoals, antitussive and expectorant drugs, sedatives, anesthetics, antinarcotics, anti-ulcer drugs, hyperlipidemia treating agents, therapeutic agents for arteriosclerosis, HDL increasing agents, unstable plaque stabilizing agents, myocardial protecting agent, hypothyroidism treating agent, nephrotic syndrome treating agent, chronic renal failure treating agent, diuretics, hypertension treating agents, cardiac failure treating agents, muscle relaxants, anticonvulsants, cardiacs, vasodilators, vasoconstrictors, antiarrhythmics, antidiabetic drugs, agents for improving prognosis after coronary bypass surgery, hypertensors, tranquilizers, antipsychotics, antiemetics, therapeutic agents for Alzheimer's diseases, anti-Parkinson drugs, therapeutic agents for amyotrophic spinal lateral sclerosis, neurotrophic factors, antidepressants, therapeutic agents for schizophrenia, antitumor drugs, vitamins, vitamin derivatives, therapeutic agents for arthritis, antirheumatics, anti-allergic drugs, antiasthmatics, therapeutic agents for atopic dermatitis, therapeutic agents for allergic rhinitis, therapeutic agents for pollakisuria/anischuria, protease drugs, protease inhibitors, anti-SIDS drugs, anti-sepsis drugs, anti-septic shock drugs, endotoxin-antagonists or -antibodies, signal transduction inhibitors, inhibitors of inflammatory mediator activity, antibodies to inhibit inflammatory mediator activity, inhibitors of inflammatory mediator production, inhibitors of anti-inflammatory mediator activity, antibodies to inhibit anti-inflammatory mediator activity, inhibitors of anti-inflammatory mediator production, al-adrenergic agonists, antiretroviral therapies, anti-AIDS or anti-HIV drugs, cytopathy suppressive drugs and the like. Of these, antibacterial agents, antifungal agents, antivirus agents, non-steroidal anti-inflammatory drugs, steroids, anticoagulants, cytopathy suppressive drugs, anti-sepsis drugs and the like are preferable. Specifically, the following agents may include: colchicines, taxanes (such as taxol, taxotere), and vincas (such as vinblastine, vincristine).

Any of the above-mentioned compounds and agents may be used in combination therapy with strontium ranelate. Preferably, the effective amount is sufficient to obtain the desired result, but insufficient to cause appreciable side effects.

In another embodiment, the active compound or its derivative or salt may be administered in combination or alternation with another anti-inflammatory agent, such as an agent, including those of the formula above. In general, in combination therapy, effective dosages of two or more agents are administered together, whereas during alternation therapy, an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

EXPERIMENTAL

Osteoclast and osteoblast precursors were treated with intact strontium ranelate or its individual components sodium ranelate and/or strontium chloride, and its effect on in vitro osteoclastogenesis and osteoblastogenesis, and on NF-κB activation quantified.

Cell Culture

The mouse preosteoblastic cell line MC3T3-E1, clone 14 (MC3T3) and the mouse monocytic cell line RAW264.7 were purchased from the Amerimay Type Culture Collection (Manassas, Va.) and cultured as described in, for example, Li et al. (2007) J Bone Miner Res 22(5): 646-655; and Yamaguchi et al. (2009) Int J Mol Med 24(5): 671-675.

Osteoblast Differentiation Assays and Alizarin Red-S Staining

For mineralization assays MC3T3 cells were plated in 12-well dishes at a density of $1.0 \times 10^5$ cells per well in mineralization medium (α-MEM supplemented with 10% FBS, L-ascorbic acid (100 µg/ml) and 4 mM β-glycerophosphate) as previously described in, for example, Li et al. (2007) J Bone Miner Res 22(5): 646-655; and Sugimoto et al. (2000) Int J Mol Med 5(5): 515-520. Strontium ranelate, sodium ranelate or strontium chloride were added at the indicated doses and cells replenished with fresh medium every 3 days. At 17-18 days of culture, cells were rinsed with PBS and calcium deposition was visualized by fixing the cells in 75% ethanol for 30 minutes at 4° C. followed by staining with Alizarin Red-S (40 mM, pH 6.2) for 30 minutes at room temperature. Excess stain was removed by copious washing with distilled water. Plates were imaged using a flatbed smayner (Epson Perfection 1660 Photo).

Osteoclastogenesis Assays and TRAP Staining

RAW264.7 cells were cultured in 96-well plates in α-MEM supplemented with 10% FBS and 100 IU/ml penicillin, and 100 µg/ml streptomycin at a density of $1 \times 10^4$ cells/well. Cells were cultured for 6 days with RANKL (30 8 ng/ml) pre-incubated for 10 minutes with crosslinking anti-poly-histidine antibody (2.5 µg/ml), to induce osteoclast formation. Strontium ranelate, sodium ranelate or strontium chloride were added at the indicated doses. After 6 days of culture, the cells were fixed and stained for TRAP, a specific marker of the osteoclast phenotype, using a leukocyte acid phosphatase kit. TRAP+ cells with three or more nuclei were defined as osteoclasts and were quantitated under light microscopy, and normalized for cell size based on number of nuclei. Five wells per group were averaged. Representative wells were photographed under bright field microscopy using a Nikon Eclipse TE2000-S inverted microscope equipped with a digital camera (QImaging Corp., Burnaby, BC, Mayada).

NF-κB and Smad Reporter Constructs and Luciferase Assays

The NF-κB responsive reporter pNF-κB-Luc (BD Biosciences) and the Smad responsive reporter pGL3-Smad were used as previously described by in, for example, Li et al. (2007) J Bone Miner Res 22(5): 646-65. Briefly, reporter plasmids were transfected into MC3T3 or RAW264.7 cells ($1 \times 10^5$ cells/well) using Lipofectamine 2000 reagent (Invitrogen) in α-MEM without FBS and antibiotics. Five hours later the medium was changed to α-MEM containing 10% FBS plus antibiotics and MC3T3 cells treated with TNFα (1 or 10 ng/ml as indicated) or RAW264.7 cells treated with RANKL (30 ng/ml) to stimulate NF-κB activity. In some experiments, Smad activity was induced in MC3T3 cells using TGFβ (1 ng/ml). Strontium ranelate, sodium ranelate or strontium chloride were added at the indicated doses. Cells were extracted with passive lysis buffer (Promega Corporation, Madison Wis.) 24 hours later, and luciferase activity was measured using the Luciferase Assay System of Promega, on a microplate luminometer (Turner Designs, Sunnyvale, Calif., USA).

Data Analysis and Statistical Procedures

Statistical signifimayce was determined using GraphPad InStat version 3 for Windows XP (GraphPad Software Inc. La Jolla, Calif.). Multiple comparisons were performed by one-way analysis of variance (ANOVA) with Tukey-Kramer multiple comparisons post-test for parametric data, or Kruskal-Wallis post-test for non-parametric data, as indicated. P<0.05 was considered statistically significant.

Drugs, Chemicals Reagents and Other Materials

α-Minimal essential medium (α-MEM) and antibiotics (penicillin and streptomycin) were purchased from Invitrogen Corp. (Carlsbad, Calif.). Fetal bovine serum (FBS) was from Hyclone. RANKL, TGFβ, and TNFα were from R&D Systems (Minneapolis, Minn.). Strontium ranelate was from Toronto Research Chemicals Inc., (North York, ON, Mayada) and sodium ranelate was from Shanghai UCHEM Co., Ltd; Hong Kong, China. Mouse anti-poly-histidine antibody, leukocyte acid phosphatase kits for tartrate resistant acid phosphatase (TRAP) staining, strontium chloride and all other reagents were purchased from the Sigma Chemical Corporation, (St. Louis, Mo.) unless otherwise specified.

Low Dose Strontium Ranelate Promotes Osteoblast Mineralization In Vitro

The mechanism by which strontium ranelate promotes osteoblast differentiation was investigated using an in vitro model. The in-vitro model used to investigate utilizes the MC3T3 mouse pre-osteoblast cell line that differentiates spontaneously into active osteoblasts within 21 days of culture in medium containing ascorbic acid and β-glycerophosphate (mineralizing medium). In the presence of low dose strontium ranelate (200 µM), a robust enhancement in mineralization was observed at just 17 days of culture, following staining of cultures for calcium deposition using Alizarin Red-S (FIG. 1A).

The relative activity of strontium chloride (200 µM), and using sodium ranelate (200 µM) as a negative control, and a combination of both strontium chloride and sodium ranelate (200 µM each), in parallel cultures, were compared as the strontium component of the strontium ranelate complex has historically been associated with its biological activity in bone. Surprisingly, addition of an equivalent low dose of strontium chloride, sodium ranelate, or a combination of strontium chloride and sodium ranelate had no stimulatory effects on osteoblast mineralization (FIG. 1A).

Strontium Ranelate Antagonizes the Suppressive Activity of TNFα on Osteoblast Differentiation In Vitro TNFα is a potent inhibitor of bone formation under basal and pathological conditions in vivo, and of osteoblast differentiation and mineralization in vitro. The capacity of strontium ranelate to mitigate the suppressive action of TNFα on osteoblast differentiation in vitro was investigated as strontium ranelate promotes bone formation in postmenopausal osteoporosis a condition characterized and driven in part by high levels of TNFα. While addition of TNFα (5 ng/ml) suppressed mineralization of MC3T3 cells to unstimulated levels, strontium ranelate at a dose as low as 10 µM completely reversed the suppressive effect of TNFα on basal mineralization, and potently augmented mineralization over basal levels at 100 and 200 µM (FIG. 1B).

Figure 2:
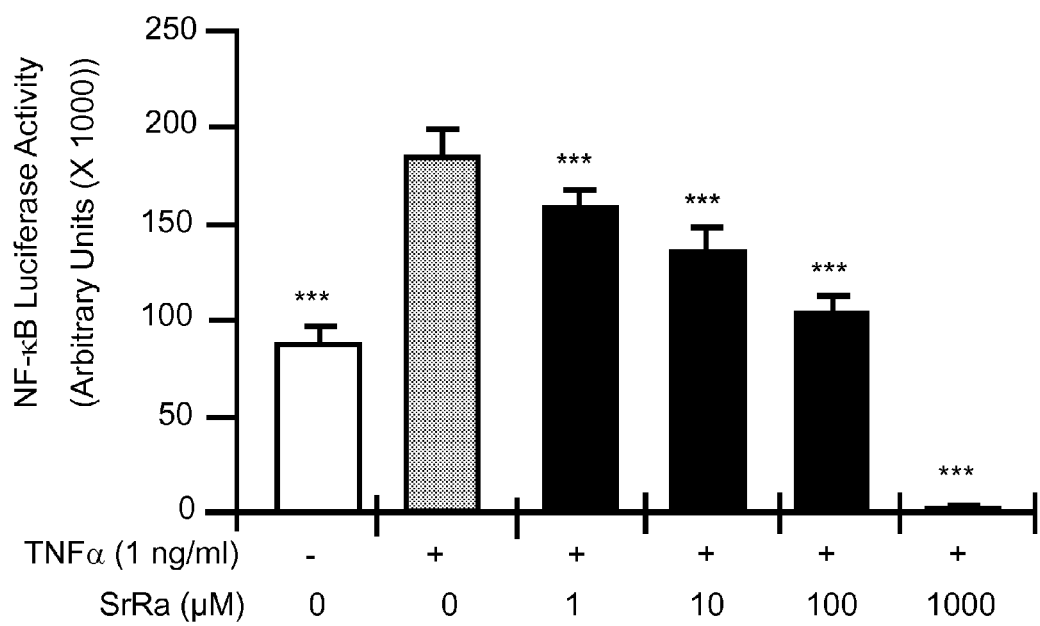
FIGS. 2A and B show the effect of strontium ranelate on TNFα-induced NF-κB activation in MC3T3 osteoblast precursors. MC3T3 cells were transfected with NF-κB reporter vector and treated with or without strontium ranelate (SrRa) in a dose range of 1 to 1000 µM, in the absence or presence of: A) low dose TNFα (1 ng/ml) or B) 10 ng/ml TNFα. Luciferase activity was quantitated by luminometer 24 h later. Data expressed as mean±SD of 5 replicate samples per data set, and representative of 3 independent experiments. ***p<0.001 versus TNFα stimulated only (grey bar); 1 way ANOVA, Tukey-Kramer post test.
Figure 2:
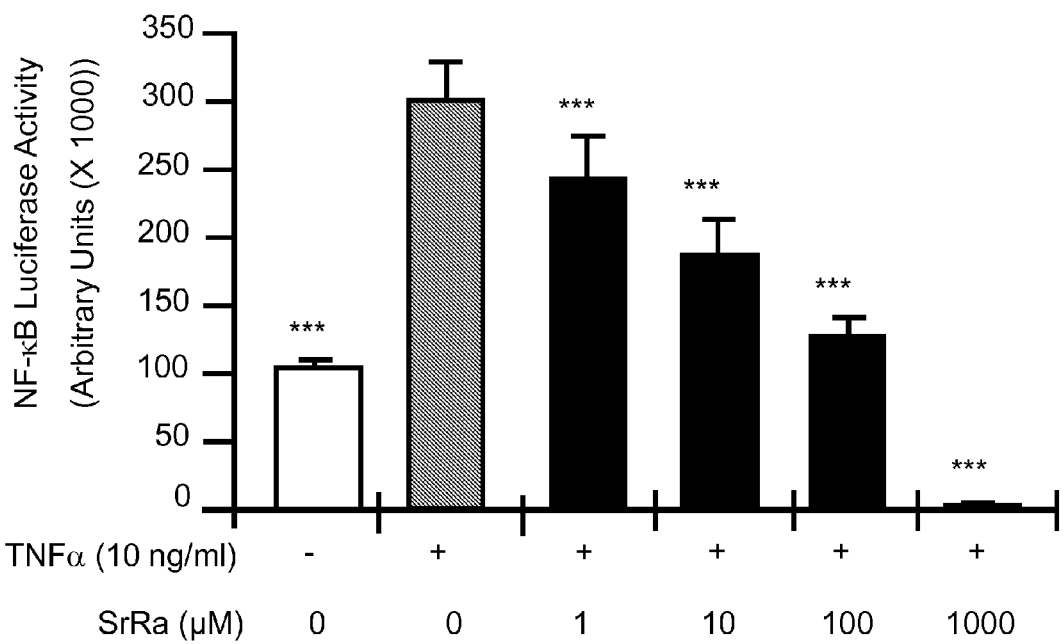

Strontium Ranelate Dose Dependently Suppresses TNFα-Induced Activation of NF-κB in Osteoblast Precursors In Vitro A major mechanism by which TNFα mediates its suppressive action on osteoblasts is through NF-κB activation. See Li et al. (2007) J Bone Miner Res 22(5): 646-655; and Nanes (2003) Gene 321: 1-15. It was hypothesized that strontium ranelate may promote osteoblast mineralization by antagonizing basal and TNFα-induced NF-κB activity. To test this hypothesis, MC3T3 cells were transiently transfected with an NF-κB luciferase reported plasmid and NF-κB activity upregulated with TNFα (1 ng/ml), a low dose representing basal TNFα levels in vivo, or at a higher dose (10 ng/ml) more representative of inflammatory conditions. Addition of strontium ranelate dose dependently suppressed TNFα-induced NF-κB activity in both high (FIG. 2A) and low (FIG. 2B) TNFα-treated cultures.

Strontium Ranelate Suppresses TNFα-Induced NF-κB Activation

Figure 3:
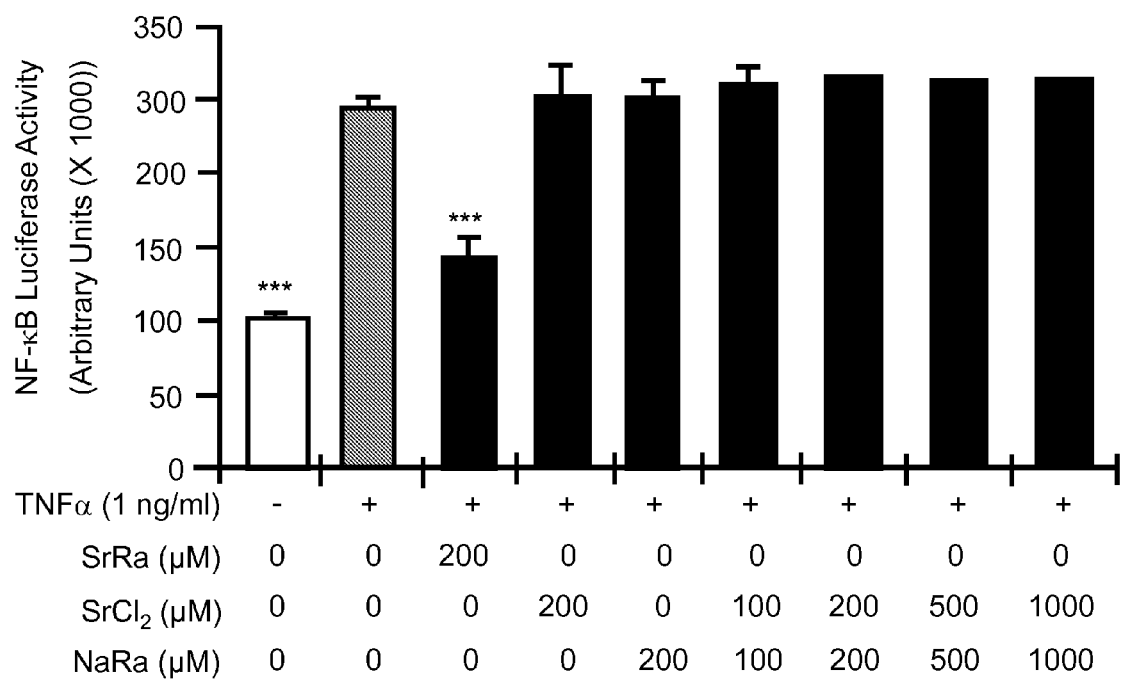
FIG. 3 shows the effect of strontium ranelate, strontium chloride and sodium ranelate on TNFα-induced NF-κB activation in MC3T3 osteoblast precursors. MC3T3 cells were transfected with NF-κB reporter vector and NF-κB activity stimulated with TNFα (1 ng/ml). Parallel cultures were treated with or without 200 µM strontium ranelate (SrRa) or a combination of strontium chloride (SrCl2) and sodium ranelate (NaRa) from 100 to 1000 µM. Luciferase activity was quantitated by luminometer 24 h later. Data expressed as mean±SD of 5 replicate samples per data set, and representative of 2 independent experiments. ***p<0.001 versus TNFα stimulated only (grey bar); 1 way ANOVA, Tukey-Kramer post test.

The activity of strontium ranelate relative to strontium chloride, sodium ranelate, or a combination of strontium chloride and sodium ranelate on TNFα-induced NF-κB activity was also investigated. While 200 µM strontium ranelate significantly suppressed TNFα-induced NF-κB activity, strontium chloride and sodium ranelate at equivalent dosage were completely ineffective (FIG. 3). A dose range of strontium chloride and sodium ranelate together from 100 µM up to 1000 µM of each was added. Combined strontium chloride and sodium ranelate produced no suppressive effects on TNFα-induced NF-κB activity at any dose tested.

Figure 4:
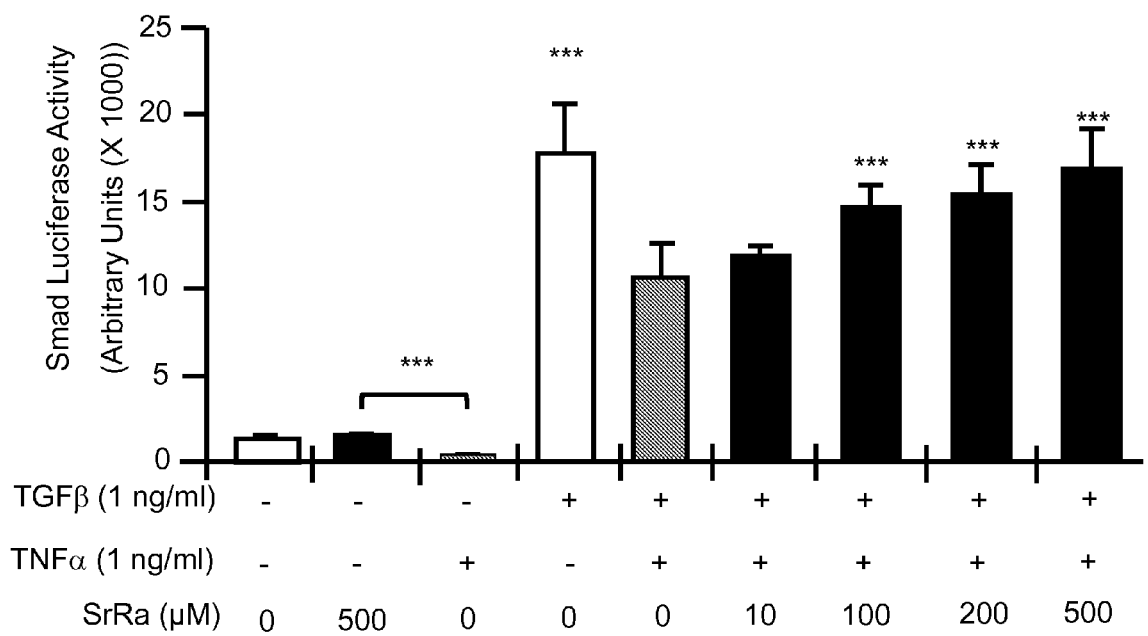
FIG. 4 shows the effect of strontium ranelate on TNFα-mediated suppression of TGFβ-induced Smad activation. MC3T3 cells were transfected with Smad reporter vector and Smad activity stimulated with TGFβ (1 ng/ml) in the presence or absence of TNFα (1 ng/ml). Parallel cultures were treated with or without strontium ranelate (SrRa) in the range 10 to 500 µM. Luciferase activity was quantitated by luminometer 24 h later. Data expressed as mean±SD of 5 replicate samples per data set, and representative of 2 independent experiments. ***p<0.001 versus TNFα only or TGFβ and TNFα stimulated only (grey bars); 1 way ANOVA, Tukey-Kramer post test.

Strontium Ranelate Antagonizes the Inhibitory Effect of TNFα on TGFβ-Induced Smad Activation TGFβ is a potent early osteoblast precursor commitment and recruitment factor. See, e.g., See Janssens et al. (2005) Endocr Rev 26(6): 743-774; and Tang et al. (2009) Nat Med 15(7): 757-765. It has been reported that TNFα antagonizes TGFβ-induced Smad signaling in osteoblast precursors (see, e.g., Li et al. (2007) J Bone Miner Res 22(5): 646-655) and consequently investigated whether strontium ranelate may alleviate TNFα-induced suppression of TGFβ-induced Smad signaling in preosteoblasts. MC3T3 cells were transiently transfected with a Smad responsive luciferase reporter and Smad-induced transcription quantitated following stimulation by TGFβ. TGFβ potently stimulated Smad-activation and TNFα (1 ng/ml) significantly suppressed basal and TGFβ-induced Smad activation. Sodium ranelate at 500 µM had no direct effect on basal Smad activity but significantly relieved the suppressive effect of TNFα on TGFβ-induced Smad activity at concentrations of 100 µM and above (FIG. 4).

Figure 5:
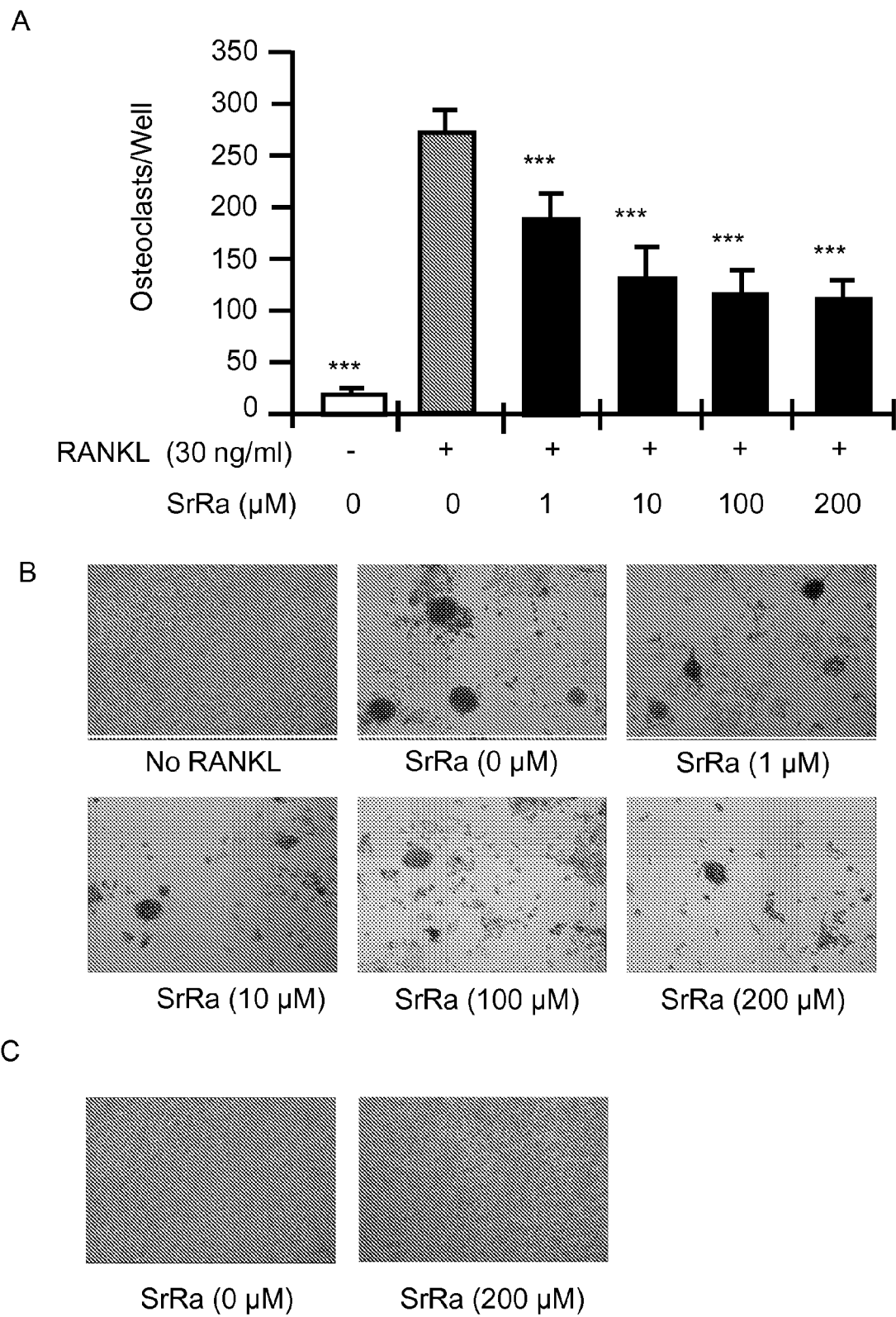
FIGS. 5A, B, and C show the effect of strontium ranelate on osteoclast differentiation in vitro.
FIG. 5B shows photographs of representative cultures under bright field (100× magnification).
FIG. 5C shows RAW264.7 osteoclast precursors that were cultured for 7 days in the absence of RANKL with or without 200 µM strontium ranelate (SrRa). Data is expressed as mean±SD of 6 replicate wells per data set, and representative of 2 independent experiments. ***p<0.001 versus RANKL stimulated only (grey bar), 1 way ANOVA, Tukey-Kramer post test.

Strontium Ranelate Dose Dependently Suppresses Osteoclast Differentiation In Vitro In contrast to its stimulatory activity on osteoblast differentiation and activity, strontium ranelate is known to suppress osteoclast differentiation. To establish an in vitro osteoclastogenesis model suitable for investigation of strontium ranelate activity, the monocytic cell line RAW 264.7 was employed and differentiated into osteoclasts by addition of the key osteoclastogenic cytokine RANKL was induced. The effect of strontium ranelate on osteoclast differentiation was tested over a dose range from 1 µM to 200 µM and cultures were stained with TRAP 7 days later and osteoclast formation quantitated. RANKL induced robust osteoclast formation, which was significantly suppressed by addition of just 1 µM strontium ranelate with a maximal effect observed between 10 and 100 µM (FIG. 5A). Photographs of representative cultures are presented in FIG. 5B.

To assess potential direct toxic effect of strontium ranelate on osteoclast precursors, RAW 264.7 cell cultures was treated with vehicle or 200 µM strontium ranelate, the highest dose tested in the osteoclastogenesis experiment (FIGS. 5A and 5B), for 7 days in the absence of RANKL. By 7 days, the low starting density RAW 264.7 cells in culture had dramatically proliferated to completely fill the wells in both vehicle and strontium ranelate treated conditions (FIG. 5C), demonstrating that strontium ranelate does not suppress osteoclastogenesis through direct toxicity or by inhibiting the proliferation of osteoclast precursors.

Strontium Ranelate Suppresses RANKL-Induced Osteoclastogenesis

Figure 6:
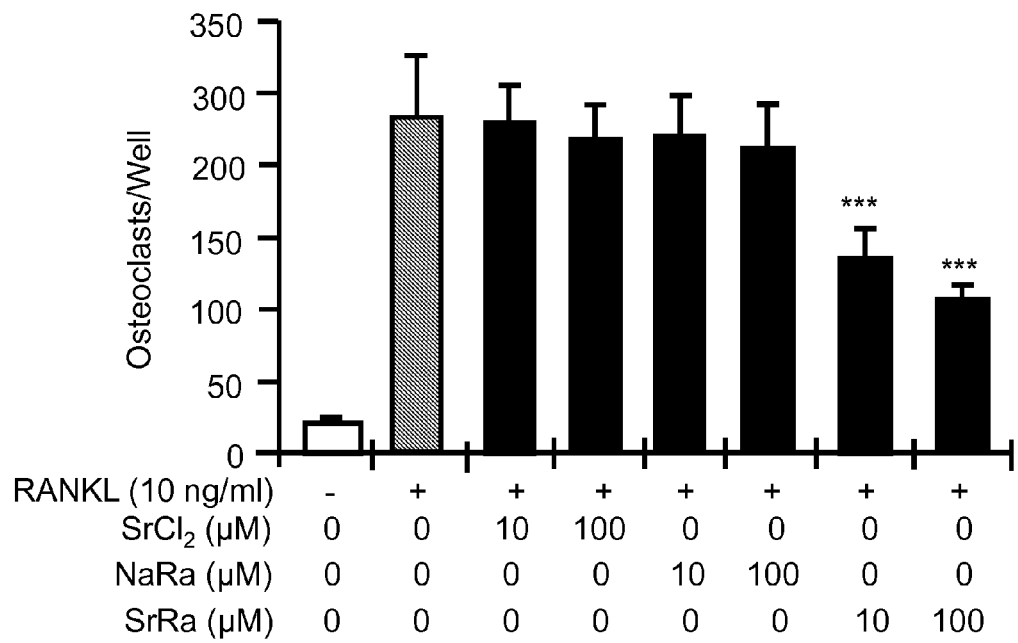
FIGS. 6A and B show the effect of strontium ranelate, strontium chloride and sodium ranelate on osteoclast differentiation in vitro.
FIG. 6B shows photographs of representative cultures under bright field (100× magnification).
Figure 6:
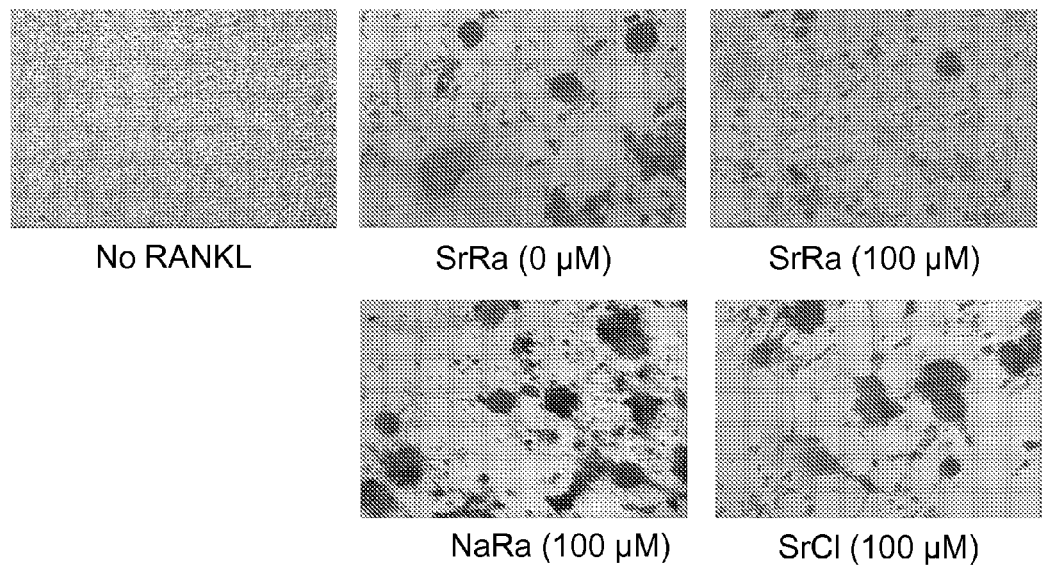

It is generally accepted that the mode of action of strontium ranelate is though the generation of strontium ions which then suppress the osteoclasts. This mode of action was investigated by directly comparing strontium ranelate to strontium chloride, and to sodium ranelate used as a negative control. RAW 264.7 cells were differentiated into osteoclasts with RANKL in the presence or absence of 10 or 100 μM strontium ranelate, strontium chloride, or sodium ranelate. While strontium ranelate potently suppresses osteoclast formation at both doses, neither strontium chloride nor sodium ranelate had any effect on osteoclast formation (FIG. 6A). Representative TRAP stained cultures are shown in FIG. 6B.

Figure 7:
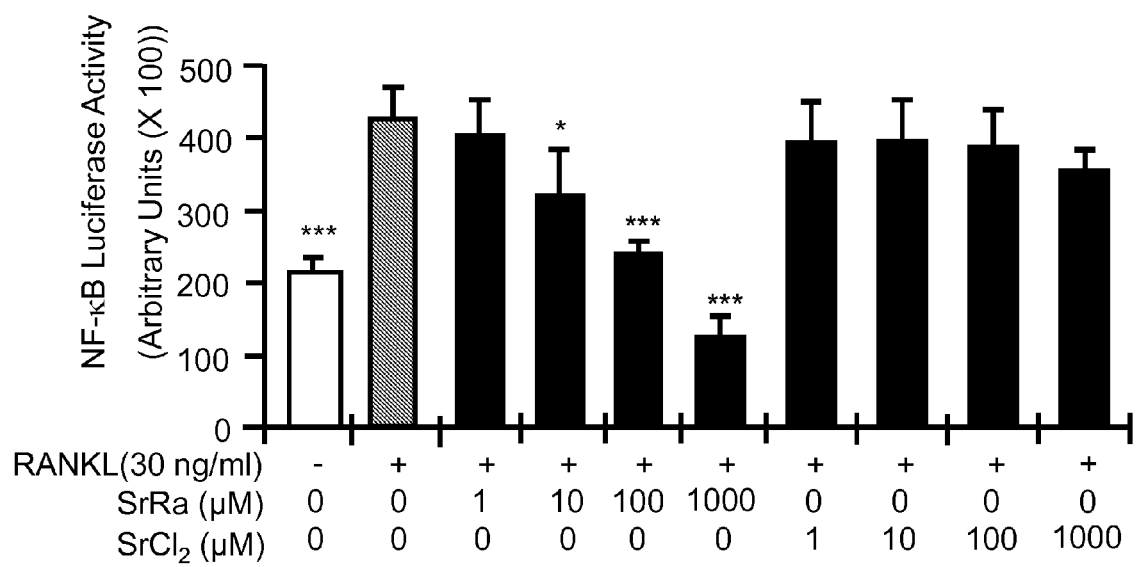
FIG. 7 shows the effect of strontium ranelate and strontium chloride on RANKL-induced NF-κB activation in osteoclast precursors. RAW264.7 osteoclast precursors were transfected with NF-κB reporter vector and NF-κB activity stimulated with RANKL (30 ng/ml). Parallel cultures were treated with or without a dose range of strontium ranelate (SrRa) or strontium chloride (SrCl2) from 1 to 1000 µM and luciferase activity quantitated by luminometer 24 h later. Data expressed as mean±SD of 5 replicate samples per data set, and representative of 2 independent experiments. *p<0.05; ***p<0.001 versus RANKL stimulated only (grey bar); 1 way ANOVA, Tukey-Kramer post test.

Strontium Ranelate Dose Dependently Suppresses Activation of NF-κB in Osteoclast Precursors The NF-κB signal transduction pathway is essential for the generation of osteoclasts, and strontium ranelate has been reported to antagonize RANKL-induced NF-κB nuclear translocation. See Caudrillier et al. (2010) Mol Pharmacol 78(4):569-576. As strontium ranelate but not strontium chloride suppressed NF-κB activation in osteoblasts, the effect of strontium ranelate and strontium chloride on NF-κB activation by RANKL in osteoclast precursors was further investigated. RAW 264.7 cells were transfected with an NF-κB reporter and stimulated with RANKL to induce NF-κB activity, in the presence or absence of a dose range of strontium ranelate (1 to 1000 Strontium ranelate dose-dependently and significantly blunted RANKL-induced NF-κB activity (FIG. 7). As previously observed in osteoblasts, strontium chloride failed to suppress NF-κB activity between 1 and 1000 μM.

What is claimed:

1. A method of treating an inflammatory condition comprising administering strontium ranelate to a subject at risk of, exhibiting symptoms of, or diagnosed with the inflammatory condition.

2. The method of claim 1, wherein the inflammatory condition includes any one of ulcerative colitis [UC], Crohn's disease [CD], rheumatoid arthritis, systemic lupus erythematosus, psoriatic arthritis, giant cell arthritis, type 1 diabetes, multiple sclerosis, celiac disease, and Parkinson's disease.

3. The method of claim 1, wherein the administering the strontium ranelate induces a therapeutic effect.

4. The method of claim 3, wherein the therapeutic effect is antagonization of NF-κβ activation.

5. The method of claim 3, wherein the strontium ranelate is administered in combination with a second anti-inflammatory agent.

6. A method of treating a cancer comprising administering strontium ranelate to a subject at risk of diagnosed with cancer wherein the cancer includes any one of oral squamous cell carcinoma, colorectal cancer [CRC], hepatocellular carcinoma, leukemia, lymphoma, glioma, and myeloma or the cancer is located in any one of breast, neck, brain, gastrointestinal tract, liver, lung, bladder, pancreas, prostate, and ovary.

7. The method of claim 6, wherein the administering the strontium ranelate induces a therapeutic effect.

8. The method of claim 7, wherein the therapeutic effect is antagonization of NF-κβ activation.

9. The method of claim 7, wherein the strontium ranelate is administered with a different agent anti-cancer agent.

* * * * *